(12) United States Patent
Zumbrum

(10) Patent No.: US 8,505,586 B2
(45) Date of Patent: Aug. 13, 2013

(54) DETACHABLE TRANSFER CONDUIT

(75) Inventor: Michael A. Zumbrum, New Oxford, PA (US)

(73) Assignee: Allpure Technologies, Inc., New Oxford, PA (US)

(*) Notice: Subject to any disclaimer, the term of this patent is extended or adjusted under 35 U.S.C. 154(b) by 132 days.

(21) Appl. No.: 13/054,749

(22) PCT Filed: Jul. 18, 2008

(86) PCT No.: PCT/US2008/070488
§ 371 (c)(1),
(2), (4) Date: Feb. 25, 2011

(87) PCT Pub. No.: WO2010/008396
PCT Pub. Date: Jan. 21, 2010

(65) Prior Publication Data
US 2011/0155274 A1    Jun. 30, 2011

(51) Int. Cl.
*F16L 55/16* (2006.01)
(52) U.S. Cl.
USPC .................. 138/99; 138/97; 285/373; 285/15
(58) Field of Classification Search
USPC ..................... 138/99, 157, 162, 97; 285/373, 285/15, 156
See application file for complete search history.

(56) References Cited

U.S. PATENT DOCUMENTS

| | | | |
|---|---|---|---|
| 2,776,473 A | 1/1957 | Dailey et al. | |
| 3,276,447 A | 10/1966 | Hamilton et al. | |
| 4,335,756 A * | 6/1982 | Sharp et al. | 138/89 |
| 5,007,666 A * | 4/1991 | Kyfes | 285/373 |
| 5,020,572 A * | 6/1991 | Hunt | 138/99 |
| 5,520,218 A | 5/1996 | Haivinka et al. | |
| 6,779,575 B1 * | 8/2004 | Arthun | 156/515 |
| RE41,169 E | 3/2010 | Arthun | |
| 7,722,733 B2 | 5/2010 | Tomasetti et al. | |
| 8,056,583 B2 * | 11/2011 | Lofving et al. | 138/99 |
| 2008/0103476 A1 | 5/2008 | Schulte et al. | |

* cited by examiner

*Primary Examiner* — Patrick F Brinson
(74) *Attorney, Agent, or Firm* — Womble Carlyle Sandridge & Rice LLP; Jacob S. Wharton

(57) ABSTRACT

A disconnect transfer conduit comprising flexible tubing; a deformable sleeve surrounding a portion of the flexible tubing; wherein the sleeve is attached to the flexible tubing and is formed of a material having plasticity such that pressure applied to the sleeve causes the sleeve to deform about and seal the flexible tubing and upon continued application of pressure to the sleeve, the sleeve and flexible tubing are cut and the sleeve retains a deformed shape substantially sealing the tubing. Also provided is a method of sealing flexible tubing comprising applying pressure to a sleeve attached to flexible tubing to deform the sleeve and seal the tubing; wherein, applying further pressure to the sleeve to cut the sleeve and tubing, thereby leaving the tubing substantially sealed where cut.

29 Claims, 2 Drawing Sheets

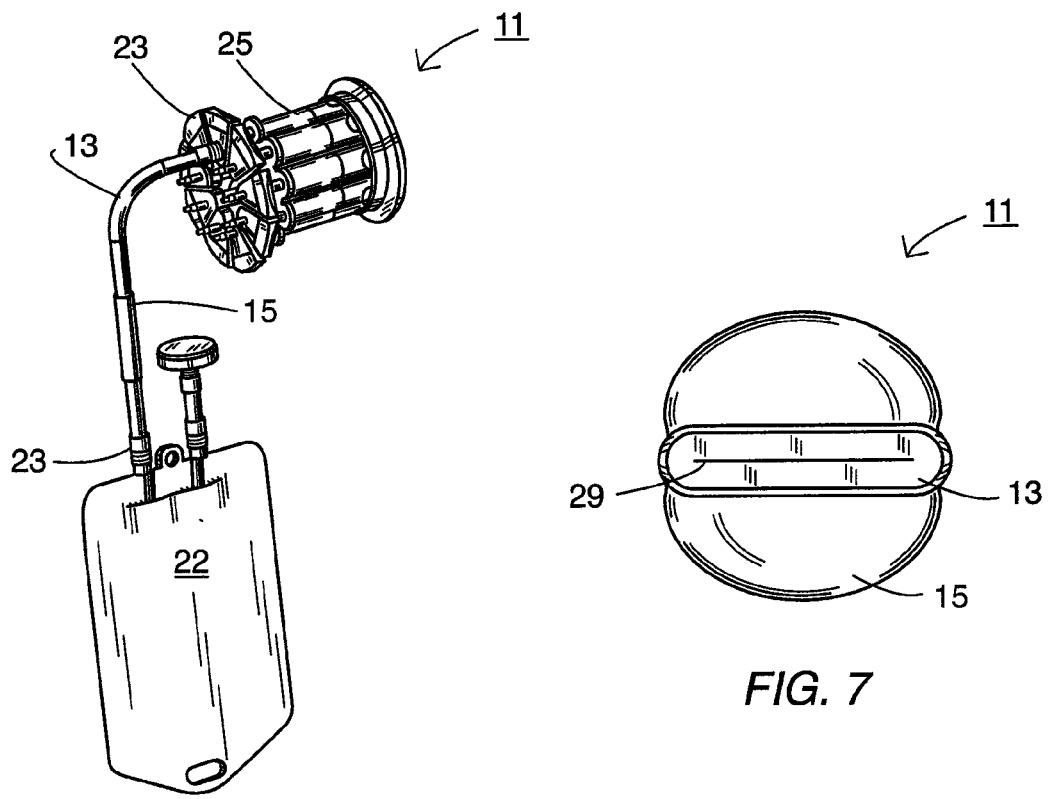
FIG. 5
FIG. 7
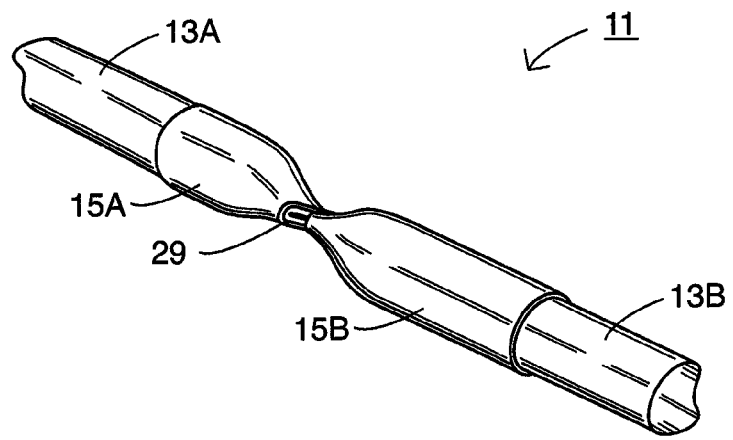
FIG. 6

DETACHABLE TRANSFER CONDUIT

TECHNICAL FIELD

This disclosure relates generally to sealing and detaching conduit, such as flexible tubing, used to transfer fluid in a substantially aseptic, hygienic, or sterile manner.

BACKGROUND

In the manufacturing and processing of many different products, it is often necessary to transfer fluid into or out of a closed processing system and do so in a substantially aseptic, hygienic, or sterile manner. In particular, the need to transfer fluid often arises in the manufacturing and processing of pharmaceuticals, biopharmaceuticals, or other biotechnology applications where processes are conducted in large process tanks, including but not limited to, the transfer of media solutions. The need for fluid transfer arises in other applications and industries as well, including but not limited to, the production of food, cosmetics, paint, chemicals, including hazardous chemicals, and the transfer and handling of semiconductor fluids. During transfers or sampling, fluid in tanks or other vessels must remain substantially free of contaminants. In addition, when making such transfers, it is desirable to keep the environment surrounding a vessel free from contamination by the contents of the vessel or a sample taken therefrom. It often is the case that throughout the manufacturing process, there is a need to take multiple samples from the fluid or, in some circumstances, add additional fluid or media to the fluid in a vessel. To accomplish a substantially aseptic, hygienic, or sterile transfer, it is desirable to control the environment through which the fluid flows. For example, the pathway from a tank to a sample container should be substantially aseptic, hygienic, or sterile along the entire pathway. Sample containers may include bags, bottles, syringes, other tanks, tubing, manifolds, or any combination thereof.

Furthermore, it is desirable to disconnect a sample container from a fluid vessel without exposing the sample to the environment or the environment to the sample. For example, it is desirable to seal and detach or disconnect conduit which may have been used to transfer fluid from a fluid vessel to a sample container. In many applications, the conduit to be sealed and disconnected is flexible tubing. In particular, it is desirable to seal and disconnect such tubing in a manner that prevents spills or leakage of the sample fluid from both ends of the disconnected tubing. It also is desirable to make a strong seal so that the sample fluid does not leak from the tubing.

It further is desirable to separate or disconnect multiple fluid vessels using a detachable transfer conduit in a quick and efficient manner. In particular, it is desirable for an operator to separate the conduit using a simple manual tool.

In view of the above, there exists a need for a conduit used to transfer fluid that is easily sealed and disconnected. Furthermore, there exists a need for such detachable transfer conduit that is pre-sterilized and disposable and capable of use in common industrial settings, such as those found in the pharmaceutical, biopharmaceutical, or other high purity industries.

SUMMARY

Briefly described, a detachable transfer conduit comprises flexible tubing; a deformable sleeve surrounding a portion of the flexible tubing. The sleeve is attached to the flexible tubing and is formed of a material having plasticity such that pressure applied to the sleeve causes the sleeve to deform about and seal the tubing before the tubing and upon continued application of pressure to the sleeve, the sleeve and flexible tubing are cut and the sleeve retains its deformed shape substantially sealing the tube. The sleeve of the detachable transfer conduit may be adhesively attached to the flexible tubing. Attaching the sleeve to the tubing prevents the sleeve from sliding on the tubing during deformation and sealing. The detachable transfer conduit may be rendered substantially aseptic and thereafter packaged to maintain the substantially aseptic state. As used herein, the term "aseptic" includes aseptic, hygienic, or sterile conditions.

In addition, the sleeve of the detachable transfer conduit is preferably made of a metal. The metal used to construct the sleeve may be selected from the group consisting of aluminum, anodized aluminum, brass, bronze, nickel-plated bronze, and stainless steel. In one embodiment, the sleeve may have a length of between about 1 and about 2 inches.

In one embodiment, the flexible tubing has an outer diameter of between about ⅛ to about 1 inch. The sleeve of the detachable transfer conduit may substantially cylindrical.

The wall of the sleeve of the detachable transfer conduit may have a wall thickness of between about 0.005 to about 0.062 inches. In one embodiment, the sleeve of the detachable transfer conduit is made from aluminum and has a wall thickness of from about 0.008 to about 0.062 inches. In another embodiment, the sleeve of the detachable transfer conduit may be made from anodized aluminum and have a wall thickness of from about 0.008 to about 0.062 inches. In yet another embodiment, the sleeve of the detachable transfer conduit may be made from bronze and have a wall thickness of from about 0.010 to about 0.032 inches. In another embodiment, the sleeve of the detachable transfer conduit may be made from nickel-plated bronze and have a wall thickness of from about 0.010 to about 0.032 inches. In another embodiment, the sleeve of the detachable transfer conduit may be made from stainless steel and have a wall thickness of from about 0.005 to about 0.032 inches.

The detachable transfer conduit may also utilize a sleeve that is attached to the flexible tubing using a silicone adhesive. In one embodiment, the silicone adhesive is curable platinum catalyzed silicone adhesive. In yet another embodiment, the silicone adhesive is moisture curable silicone adhesive. In another embodiment, the sleeve may be attached to the flexible tubing using a hot melt adhesive. The sleeve of the detachable transfer conduit may be attached to the flexible tubing using an adhesive selected from the group consisting of cyanoacrylate, epoxy, and urethane. In one embodiment, the flexible tubing of the detachable transfer conduit comprises thermoplastic elastomer tubing. The thermoplastic elastomer may be selected from group consisting of styrene isobutylene copolymer and ethylene propylene copolymers blended with polypropylene. In another embodiment, the flexible tubing of the disconnect assembly comprises thermoplastic polymer tubing. In yet another embodiment, the flexible tubing comprises thermoset elastomer tubing. The thermoplastic polymer may be selected from the group consisting of polyvinyl chloride (PVC) or a flexible polyolefin. The thermoset elastomer may be selected from the group consisting of silicone, phenyl silicone, fluoroelastomer (FKM), perfluoroelastomer (FFKM), or perfluoropolyether. The detachable transfer conduit may also comprise a primer between the flexible tubing and the adhesive.

In another embodiment of the detachable transfer conduit, the flexible tubing may be adhesively attached to a sleeve and, where upon application of pressure to the sleeve, the sleeve deforms and seals the tubing such that upon cutting of the sleeve, the tubing remains substantially sealed where cut.

Also provided is a method of sealing flexible tubing comprising applying pressure to a sleeve attached to flexible tubing to deform the sleeve and seal the tubing and, wherein applying further pressure to the sleeve cuts the sleeve and tubing, thereby leaving the tubing substantially sealed where cut. In one embodiment, the method of sealing the flexible tubing, the pressure applied to seal the tubing and the pressure applied to cut the tubing and sleeve is applied simultaneously.

The invention will be better understood and appreciated upon review of the detailed description set forth below when taken in conjunction with the accompanying drawing figures, described briefly below. According to common practice, the various features of the drawings may not be drawn to scale. Dimensions and relative sizes of various features and elements in the drawings may be shown enlarged or reduced to illustrate more clearly the embodiments of the invention.

BRIEF DESCRIPTION OF THE DRAWINGS

FIG. 5 is a perspective view of an embodiment of a detachable transfer conduit connected to a sampling device and sample container.
FIG. 6 is a perspective view of an embodiment of deformed and detached sleeve and flexible tubing.
FIG. 7 is an end view of an embodiment of a deformed and detached sleeve and flexible tubing.

DETAILED DESCRIPTION

Figure 1:
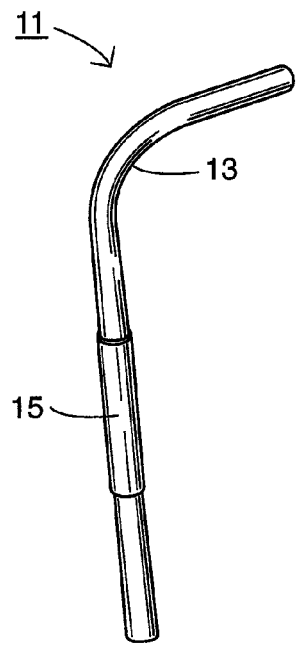
FIG. 1 is a perspective view of an embodiment of a detachable transfer conduit.

Referring now in more detail to the figures, FIG. 1 is a perspective view of an embodiment of a detachable transfer conduit 11. The detachable transfer conduit 11 comprises flexible tubing 13 and a deformable sleeve 15. The deformable sleeve 15 surrounds a portion of the flexible tubing 13. The deformable sleeve 15 is attached to the flexible tubing 13. The deformable sleeve 15 may be attached at any suitable location along the flexible tubing 13. In a preferred embodiment, the deformable sleeve 15 is attached to the flexible tubing 13 at a location that facilitates substantially sealing, cutting, and detaching the deformable sleeve 15 once cut. In yet another preferred embodiment, the deformable sleeve 15 is adhesively attached to the flexible tubing 13. Attaching the sleeve 15 to the flexible tubing 13 prevents the sleeve 15 from slipping on the tubing away from the point where the flexible tubing 13 is substantially sealed and cut and thus maintains the seal in the flexible tubing 13. If the sleeve 15 were not attached to the flexible tubing 13, the sleeve would slip or pull away from the location on the flexible tubing 13 that was sealed, thus breaking the seal and allowing the flexible tubing 13 to open.

Figure 2:
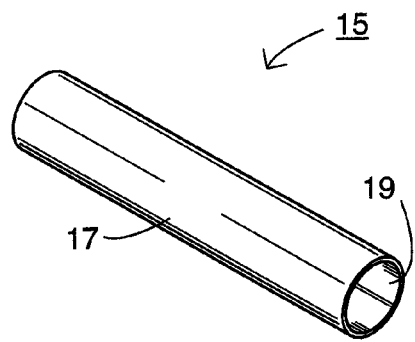
FIG. 2 is a perspective view of an embodiment of a deformable sleeve.

FIG. 2 depicts an embodiment of a deformable sleeve 15. The deformable sleeve comprises a wall 17 having an inner surface 19. In a preferred embodiment, the deformable sleeve is made of a metal. The metal used to make the deformable sleeve may be selected from the group consisting of aluminum, anodized aluminum, brass, bronze, nickel-plated bronze, and stainless steel. However, any suitable material may be used, including metals not listed above. Regardless of the material from which the deformable sleeve 15 is constructed, the material has a plasticity such that pressure applied to the flexible tubing 13 at the location of the deformable sleeve 15 causes the sleeve to deform about and substantially seal the flexible tubing 13 before the flexible tubing 13 and deformable sleeve 15 are cut by continued application of pressure. The material also has plasticity such that once cut the deformable sleeve 15 retains its deformed shape and thus substantially seals the flexible tubing 13. In a preferred embodiment, the deformable sleeve 15 has a length of between about 1 and about 2 inches. However, the deformable sleeve 15 may be of any suitable length.

Figure 3:
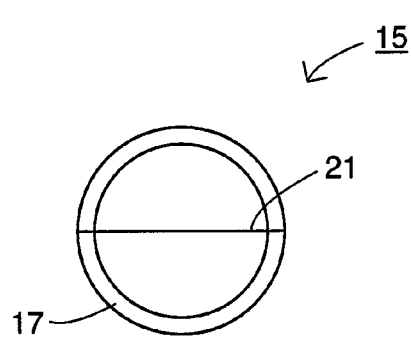
FIG. 3 is an end view of an embodiment of a deformable sleeve.

FIG. 3 is an end view of an embodiment of a deformable sleeve 15. As shown in FIG. 3, the deformable sleeve 15 has an outer diameter 21. FIG. 3 also depicts the wall 17 of the deformable sleeve 15. In a preferred embodiment, the deformable sleeve 15 is substantially cylindrical. However, the sleeve may be shaped in any suitable manner that corresponds with the profile of the flexible tubing 13, and may, for example, have an oval shaped profile or any other profile.

It is understood that the deformable sleeve 15 may be made from a variety of materials or combination of materials, preferably metals, and that depending on the materials used, the wall thickness varies. In one embodiment, the wall 17 has a thickness of between about 0.008 and about 0.062 inches. In a preferred embodiment, the deformable sleeve 15 is made from aluminum and has a wall thickness of from about 0.008 to about 0.062 inches. In another preferred embodiment, the deformable sleeve 15 is made from anodized aluminum and has a wall thickness of from about 0.008 to about 0.062 inches. In yet another preferred embodiment, the deformable sleeve 15 is made from bronze and has a wall thickness of from about 0.010 to about 0.032 inches. Depending on the metal selected, the wall thickness will vary in order to maintain plasticity in the deformable sleeve 15 such that it may be substantially sealed and cut by application of a reasonable amount of pressure. A reasonable amount of pressure would be, for example, that which may be applied by an operator using a manually operated cutting tool.

Figure 4:
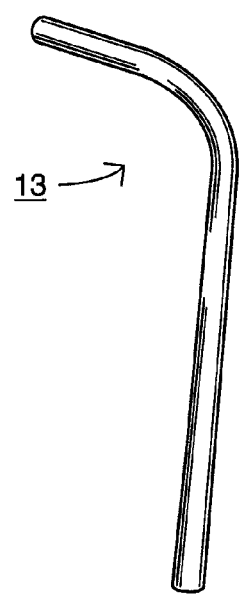
FIG. 4 is a perspective view of an embodiment of flexible tubing.

FIG. 4 depicts an embodiment of flexible tubing 13. As shown in FIG. 4, the flexible tubing 13 is angled. However, the flexible tubing 13 may be straight or have any other suitable configuration. In one embodiment, the flexible tubing 13 is thermoplastic elastomer tubing such as a styrene isobutylene copolymer (C-Flex®) or ethylene propylene copolymers blended with polypropylene (Santoprene®). In another embodiment, the flexible tubing 13 is made from a thermoplastic polymer such as polyvinyl chloride (PVC) or a flexible polyolefin such as Engage®. In another embodiment, the flexible tubing 13 is made from a thermoset elastomer such as silicone, fluoro silicone, phenyl silicone, fluoroelastomer (FKM), perfluoroelastomer (FFKM), or perfluoropolyether (Sifel®). In yet another embodiment, the flexible tubing 13 is made from a composite material such as a PTFE lined elastomer tube (SmartShield™ tubing), perfluoroalkoxy lined thermoplastic tubing (Bev-a-line®). Other material suitable to perform as flexible tubing 13 may be selected and the listing above is not limiting.

The deformable sleeve 15 may be attached to the flexible tubing 13 in a variety of ways. In a preferred embodiment, the deformable sleeve 15 is attached to the flexible tubing 13 with a silicone adhesive. In another preferred embodiment, the silicone adhesive is curable platinum catalyzed silicone adhesive. In yet another preferred embodiment, the silicone adhesive is moisture curable silicone adhesive. In one preferred embodiment, the flexible tubing 13 is primed before application of the adhesive and attaching to the deformable sleeve 15, thereby leaving a layer of primer between the flexible tubing 13 and the deformable sleeve 15. The primer may also operate to substantially seal the tubing upon the application of pressure and, ultimately, cutting of the flexible tubing 13 and deformable sleeve 15.

In another embodiment of the detachable transfer conduit, the deformable sleeve 15 is attached to the flexible tubing 13 with a hot melt adhesive. This is particularly useful for thermoplastic elastomer tubing. In yet another embodiment of the detachable transfer conduit, the deformable sleeve 15 is attached to the flexible tubing 13 using an adhesive selected from the group consisting of cyanoacrylate, epoxy, and urethane. These adhesives are particularly useful for thermoset elastomer tubing.

In another embodiment of the detachable transfer conduit 11, there is provided a flexible tubing 13 adhesively attached to a deformable sleeve 15 and, where upon application of pressure to the deformable sleeve 13, the deformable sleeve 15 deforms and substantially seals the flexible tubing 13 and upon application of additional pressure the flexible tubing 13 and deformable sleeve 15 are severed or cut, leaving the flexible tubing 13 sealed where cut.

FIG. 5 illustrates a detachable transfer conduit 11 in use with a sampling device 25 and a sample container 22. The detachable transfer conduit 11 is connected both to the sampling device 25 and the sample container 22 by way of collars 23. As shown in FIG. 5, the detachable transfer conduit comprises the flexible tubing 13 and deformable sleeve 15. In use, an operator may draw a sample from a media receptacle (not shown), such as a tank using sample device 25, thereby filling sample container 22 with a sample. At that point, the operator must disconnect the sample container 22 from the flexible tubing attached to the sampling device 25. The operator may apply pressure to deformable sleeve 15, which is adhesively attached to flexible tubing 13, and deform the sleeve 15 thereby sealing the flexible tubing 13. The operator may then apply additional pressure to cut the deformable sleeve 15 and the flexible tubing 13 thereby cutting the deformable sleeve 15 and the flexible tubing 13 and leaving the flexible tubing 13 substantially sealed where cut. In a preferred embodiment, the operator quickly applies pressure that substantially seals and then immediately cuts the deformable sleeve 15. The pressure may be applied with a tool such as a pair of snips or wire cutters or any other tool sufficient to crimp and cut the deformable sleeve 15 and flexible tubing 13.

FIG. 6 provides an embodiment of a detachable transfer conduit 11 that has been cut or severed. In this cut state, there is provided two pieces of the deformable sleeve 15A and 15B. Likewise, there is now provided two pieces of flexible tubing 13A and 13B. One piece of tubing may remain attached to a sampling device 25 such as the one shown in FIG. 5 while the other piece of flexible tubing is removed from the sampling area with sample container 22 attached. Once cut, the crimped flexible tubing 13 and deformable sleeve 15 form a seal 29. Due to the physical properties of the flexible tubing 13 and deformable sleeve 15 described in detail above, the flexible tubing 13 and deformable sleeve 15 remain substantially sealed thereby preventing fluid or other media from escaping the flexible tubing 13.

FIG. 7 is an end view of a detachable transfer conduit 11 that has been cut or severed. In the cut state, the deformed or crimped sleeve 15 compresses the flexible tubing 13 to form a seal 29.

The detachable transfer conduit 11 may be assembled and then the entire device or components thereof may be rendered aseptic by, for example, gamma radiation. In another embodiment, the detachable transfer or components thereof may be rendered aseptic by exposure to steam above 121° C. for a period of time long enough to eliminate microorganisms. In yet another embodiment, the detachable transfer conduit or components thereof may be rendered aseptic by chemical treatment, such as with ethylene oxide (ETO). In a preferred embodiment, the detachable transfer conduit is rendered aseptic by gamma radiation. Once rendered aseptic, the detachable transfer conduit may be appropriately packaged and stored to maintain the aseptic state until ready for use.

All dimensional information presented herein and included in the drawings is intended to be illustrative and not intended to limit the scope of the invention.

The foregoing descriptions of detachable transfer conduit illustrate and describe various embodiments considered to represent best modes of carrying out the invention. As various changes can be made in the above embodiments without departing from the scope of the detachable transfer conduit disclosed and claimed herein, it is intended that all matter contained in the above description or shown in the accompanying drawings shall be interpreted as illustrative and not limiting. Furthermore, the scope of the invention covers various modifications, combinations, alterations, etc., of the above-described embodiments that all are within the scope of the claims. Additionally, the disclosure shows and describes only selected embodiments of the invention, but the invention is capable of use in various other combinations, modifications, and environments and is capable of changes or modifications within the scope of the inventive concept as expressed herein, commensurate with the above teachings, and/or within the skill or knowledge of artisans in the relevant art. Furthermore, certain features and characteristics of each embodiment may be selectively interchanged and applied to other illustrated and non-illustrated embodiments of the invention without departing from the scope of the invention.

What is claimed is:

1. A disconnect transfer conduit comprising:
   flexible tubing; and
   a deformable sleeve adhesively attached to and surrounding a portion of the flexible tubing;
   wherein the sleeve and adhesive are formed of materials having plasticity such that pressure applied to the sleeve causes the sleeve and adhesive to deform about and seal the flexible tubing and upon continued application of pressure to the sleeve, the sleeve, adhesive, and flexible tubing are cut and the sleeve retains a deformed shape substantially sealing the tubing.

2. The disconnect transfer conduit of claim 1, wherein the sleeve is made of a metal.

3. The disconnect transfer conduit of claim 2, wherein the sleeve is made of a metal selected from the group consisting of aluminum, anodized aluminum, brass, bronze, nickel-plated bronze, and stainless steel.

4. The disconnect transfer conduit of claim 1, wherein the sleeve is a length of between about 1 and about 2 inches long.

5. The disconnect transfer conduit of claim 1, wherein the flexible tubing has an outer diameter of between about ⅛ to about 1 inch.

6. The disconnect transfer conduit of claim 1, wherein the sleeve is substantially cylindrical.

7. The disconnect transfer conduit of claim 6, wherein the sleeve has as wall thickness of between about 0.005 to about 0.062 inches.

8. The disconnect transfer conduit of claim 7, wherein the sleeve is made from aluminum and has a wall thickness of from about 0.008 to about 0.062 inches.

9. The disconnect transfer conduit of claim 1, wherein the sleeve is made from anodized aluminum and has a wall thickness of from about 0.008 to about 0.062 inches.

10. The disconnect transfer conduit of claim 7, wherein the sleeve is made from bronze and has a wall thickness of from about 0.010 to about 0.032 inches.

11. The disconnect transfer conduit of claim 7, wherein the sleeve is made from nickel-plated bronze and has a wall thickness of from shout 0.010 to about 0.032 inches.

12. The disconnect transfer conduit of claim 7, wherein the sleeve is made from stainless steel and has a wall thickness of from about 0.005 to about 0.032 inches.

13. The disconnect transfer conduit of claim 1, wherein the sleeve is attached to the flexible tubing with a silicone adhesive.

14. The disconnect transfer conduit of claim 13, wherein the silicone adhesive comprises a curable platinum catalyzed silicone adhesive.

15. The disconnect transfer conduit of claim 13, wherein the silicone adhesive comprises a moisture curable silicone adhesive.

16. The disconnect transfer conduit of claim 1, wherein the sleeve is attached to the flexible tubing with a hot melt adhesive.

17. The disconnect transfer conduit of claim 1, wherein the sleeve is attached to the flexible tubing using an adhesive selected from the group consisting of cyanoacrylate, epoxy, and urethane.

18. The disconnect transfer conduit of claim 1, wherein the flexible tubing comprises a thermoplastic elastomer tubing.

19. The disconnect transfer conduit of claim 18, wherein the flexible tubing is constructed from material selected from the group consisting of styrene isobutylene copolymer and ethylene propylene copolymers blended with polypropylene.

20. The disconnect transfer conduit of claim 1, wherein the flexible tubing comprises thermoplastic polymer tubing.

21. The disconnect transfer conduit on claim 20, wherein the flexible tubing is constructed from material selected from the group consisting of polyvinyl chloride (PVC) or a flexible polyolefin.

22. The disconnect transfer conduit of claim 1, wherein the flexible tubing comprises thermoset elastomer tubing.

23. The disconnect transfer conduit of claim 22, wherein the flexible tubing is constructed from material selected from the group consisting of silicone, phenyl silicone, fluoroelastomer (FKM), perfluoroelastomer (FKM), or perfluoropolyether.

24. The disconnect transfer conduit of claim 1, wherein the flexible tubing further comprises a primer between the flexible tubing and the adhesive.

25. The disconnect transfer conduit of claim 1, wherein the conduit is substantially aseptic.

26. The disconnect transfer conduit of claim 25, wherein the conduit is pre-sterilized and packaged to maintain a substantially aseptic condition until use.

27. A disconnect transfer conduit comprising flexible tubing adhesively attached to a sleeve, wherein, upon application of pressure to the sleeve, the sleeve deforms and seals the tubing such that upon cutting of the sleeve, the tubing remains substantially sealed where cut.

28. A method of sealing flexible tubing comprising:
applying pressure to a sleeve adhesively attached to surrounding flexible tubing to deform the sleeve and seal the tubing;
wherein, applying further pressure to the sleeve cuts the sleeve, adhesive, and tubing thereby leaving the tubing substantially sealed where cut.

29. The method of claim 28 wherein the pressure to seat and the pressure to cut is applied simultaneously.

\* \* \* \* \*